US00RE47596E

(19) United States
(12) Reissued Patent
Müller et al.

(10) Patent Number: US RE47,596 E
(45) Date of Reissued Patent: Sep. 10, 2019

(54) DISPLAY SCREEN WITH AN ANIMATED GRAPHICAL USER INTERFACE FOR MEDICAL SOFTWARE

(71) Applicant: Brainlab AG, Munich (DE)

(72) Inventors: Annika Müller, Munich (DE); Julian Ang, Munich (DE)

(73) Assignee: Brainlab AG, Munich (DE)

(21) Appl. No.: 29/666,992

(22) Filed: Oct. 17, 2018

Related U.S. Patent Documents

Reissue of:
(64) Patent No.: Des. 814,480
Issued: Apr. 3, 2018
Appl. No.: 29/585,374
Filed: Nov. 23, 2016

(30) Foreign Application Priority Data

May 23, 2016 (EM) ..... 003147651

(51) LOC (12) Cl. ..... 14-04
(52) U.S. Cl.
USPC ..... D14/485
(58) Field of Classification Search
USPC ..... D14/485–495
CPC .. G06F 3/048; G06F 3/04842; G06F 3/04847; G06F 3/0481; G06F 17/211; G06F 17/212
See application file for complete search history.

(56) References Cited

U.S. PATENT DOCUMENTS 6,232,971 B1 * 5/2001 Haynes ..... G06F 9/4443 75/800
D522,015 S * 5/2006 Cummins ..... D14/487
D529,507 S * 10/2006 Cummins ..... D14/485
D550,228 S * 9/2007 Bandman ..... D14/486
D615,099 S * 5/2010 Barcheck ..... D14/492
D622,730 S * 8/2010 Krum ..... D14/486
D626,141 S * 10/2010 Schilling ..... D14/488
D636,779 S * 4/2011 Boush ..... D14/486
D640,264 S * 6/2011 Fujii ..... D14/486
D652,047 S * 1/2012 Forsythe ..... D14/485
D652,048 S * 1/2012 Joseph ..... D14/485
D658,670 S * 5/2012 Ray ..... D14/486
D658,672 S * 5/2012 Ray ..... D14/486
D664,970 S * 8/2012 Ray ..... D14/486
D664,982 S * 8/2012 Rai ..... D14/488

(Continued)

*Primary Examiner* — Philip S Hyder
(74) *Attorney, Agent, or Firm* — Middleton Reutlinger

(57) CLAIM

The ornamental design for a display screen with an animated graphical user interface for medical software, as shown and described.

DESCRIPTION

FIG. 1 is a first image of a display screen with an animated graphical user interface for medical software showing the new design;
FIG. 2 is a second image thereof;
FIG. 3 is a third image thereof;
FIG. 4 is a fourth image thereof;
FIG. 5 is a fifth image thereof;
FIG. 6 is a sixth image thereof; and,
FIG. 7 is a seventh image thereof.
The broken lines showing a display screen and portions of the graphical user interface illustrate portions of the article and form no part of the claimed design.
The appearance of the animated graphical user interface transitions from FIGS. 1-7. The process or period in which one image transitions to another forms no part of the claimed design.

1 Claim, 7 Drawing Sheets

Matter enclosed in heavy brackets [ ] appears in the original patent but forms no part of this reissue; matter printed in italics indicates the additions made by reissue.

(AMENDED)

(56) References Cited

U.S. PATENT DOCUMENTS

D667,417 S * 9/2012 Long ..... D14/486
D670,725 S * 11/2012 Mori ..... D14/486
D673,577 S * 1/2013 Cojuangco ..... D14/486
D678,302 S * 3/2013 Trumble ..... D14/486
D681,050 S * 4/2013 Ray ..... D14/486
D681,666 S * 5/2013 Donahue ..... D14/488
D682,307 S * 5/2013 Donahue ..... D14/488
D682,878 S * 5/2013 Donahue ..... D14/488
D685,814 S * 7/2013 Bork ..... D14/486
D691,159 S * 10/2013 Boush ..... D14/486
D692,455 S * 10/2013 Dhanani ..... D14/487
D694,252 S * 11/2013 Helm ..... D14/485
D705,797 S * 5/2014 Varon ..... D14/486
D709,904 S * 7/2014 Wong ..... D14/486
D716,833 S * 11/2014 Donahue ..... D14/486
D717,331 S * 11/2014 Lin ..... D14/486
D718,776 S * 12/2014 Hobbs ..... D14/486
D719,963 S * 12/2014 Hobbs ..... D14/486
D726,745 S * 4/2015 Park ..... D14/486
D726,746 S * 4/2015 Poston ..... D14/486
D728,578 S * 5/2015 Kito ..... D14/440
D728,586 S * 5/2015 Konno ..... D14/485
D731,513 S * 6/2015 Donahue ..... D14/486
D733,173 S * 6/2015 Donahue ..... D14/486
D733,727 S * 7/2015 Cojuangco ..... D14/486
D737,291 S * 8/2015 Donahue ..... D14/486
D737,304 S * 8/2015 Urdan ..... D14/486
D737,305 S * 8/2015 Scazafavo ..... D14/486
D737,306 S * 8/2015 Scazafavo ..... D14/486
D739,866 S * 9/2015 Urdan ..... D14/486
D740,842 S * 10/2015 Liu ..... D14/486
D740,847 S * 10/2015 Yampolskiy ..... D14/486
D741,884 S * 10/2015 Lee ..... D14/486
D743,983 S * 11/2015 Seo ..... D14/486
D745,017 S * 12/2015 Ku ..... D14/485
D745,550 S * 12/2015 Sanderson ..... D14/488
D745,877 S * 12/2015 Supino ..... D14/485
D746,845 S * 1/2016 Archer ..... D14/486
D746,847 S * 1/2016 Bauer ..... D14/486
D748,661 S * 2/2016 Addaguduru ..... D14/486
D749,108 S * 2/2016 Bauer ..... D14/486
D749,110 S * 2/2016 Noack ..... D14/486
D750,099 S * 2/2016 Seo ..... D14/485
D757,070 S * 5/2016 Dziuba ..... D14/486
D757,759 S * 5/2016 Ku ..... D14/485
D757,760 S * 5/2016 Ku ..... D14/485
D760,288 S * 6/2016 Kendler ..... D14/492
D765,694 S * 9/2016 Knapp ..... D14/486
D766,949 S * 9/2016 Johnson ..... D14/486
D770,495 S * 11/2016 Knapp ..... D14/486
D771,669 S * 11/2016 Rodriguez ..... D14/486
D771,692 S * 11/2016 Rodriguez ..... D14/486
D772,890 S * 11/2016 Bauer ..... D14/485
D772,900 S * 11/2016 Kim ..... D14/486
D773,505 S * 12/2016 Knapp ..... D14/486
D774,050 S * 12/2016 Knapp ..... D14/485
D774,077 S * 12/2016 Donnelly ..... D14/488
D774,525 S * 12/2016 Seo ..... D14/486
D775,653 S * 1/2017 Hoffman ..... D14/486
D783,656 S * 4/2017 Blaas ..... D14/486
D801,372 S * 10/2017 Higuchi ..... D14/486
2006/0123355 A1* 6/2006 Christiansen ..... G06F 3/0481 715/781
2009/0240527 A1* 9/2009 Bluth ..... A61B 5/02055 705/3
2009/0260022 A1* 10/2009 Louch ..... B60K 35/00 719/328
2010/0005008 A1* 1/2010 Duncker ..... G06F 17/30893 705/26.1
2010/0005411 A1* 1/2010 Duncker ..... G06F 17/30873 715/769
2011/0283242 A1* 11/2011 Chew ..... G06F 17/30716 715/863
2014/0245171 A1* 8/2014 Jaycobs ..... G06F 3/04842 715/746
2015/0213211 A1* 7/2015 Zaleski ..... G06F 19/3406 715/753

* cited by examiner

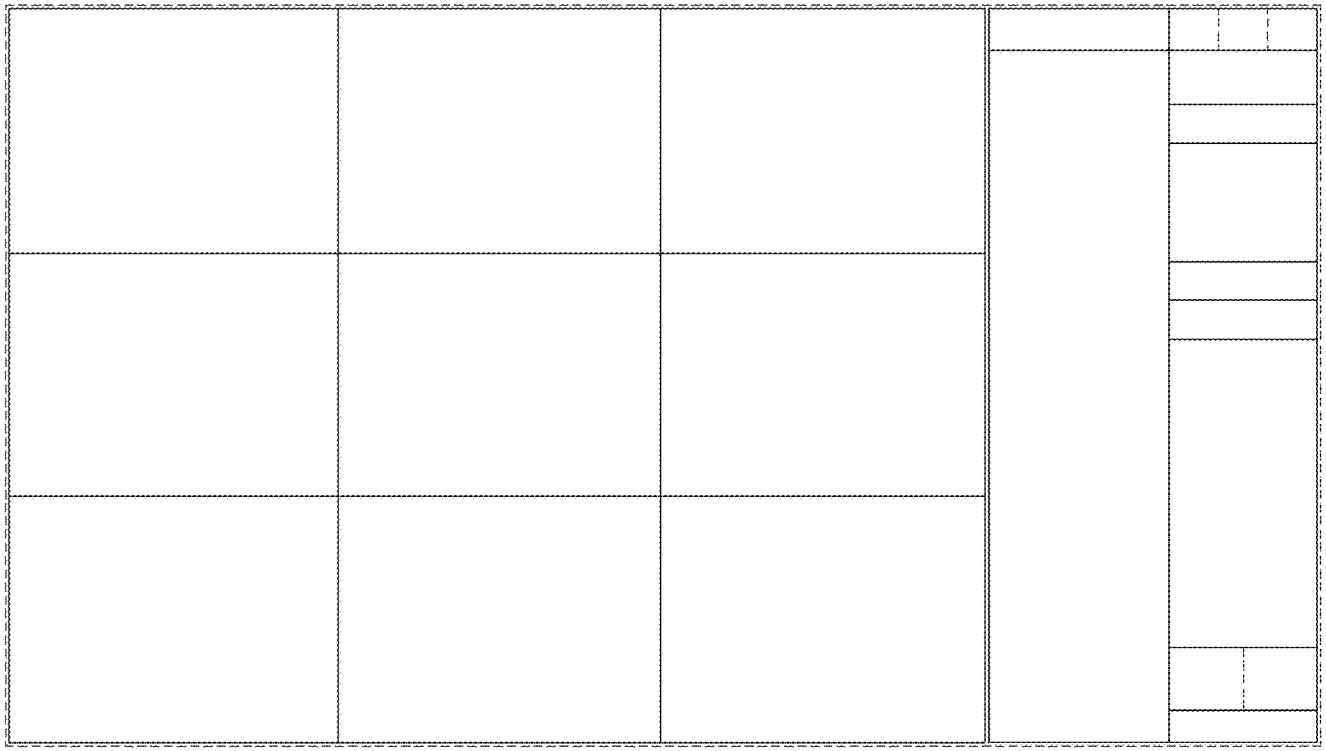
(AMENDED) FIG. 1

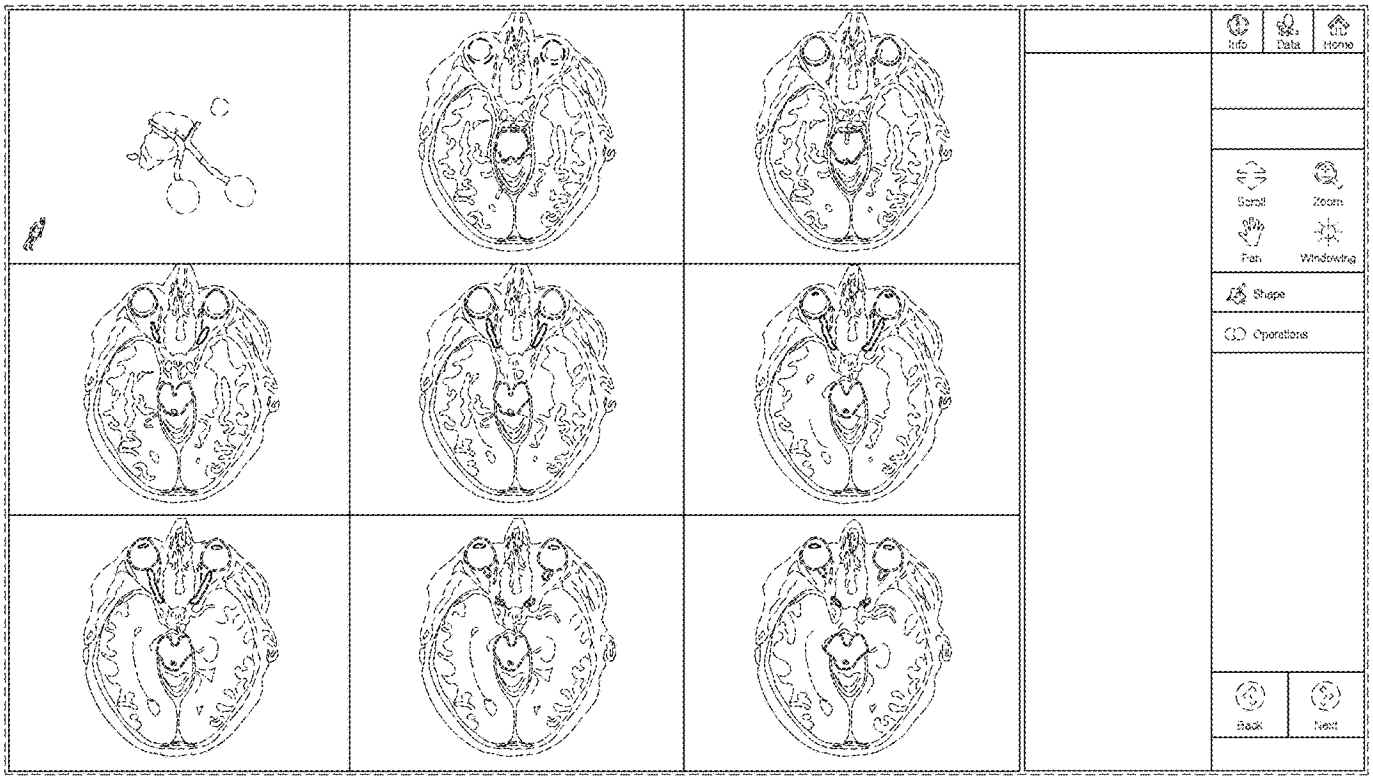
(AMENDED) FIG. 2

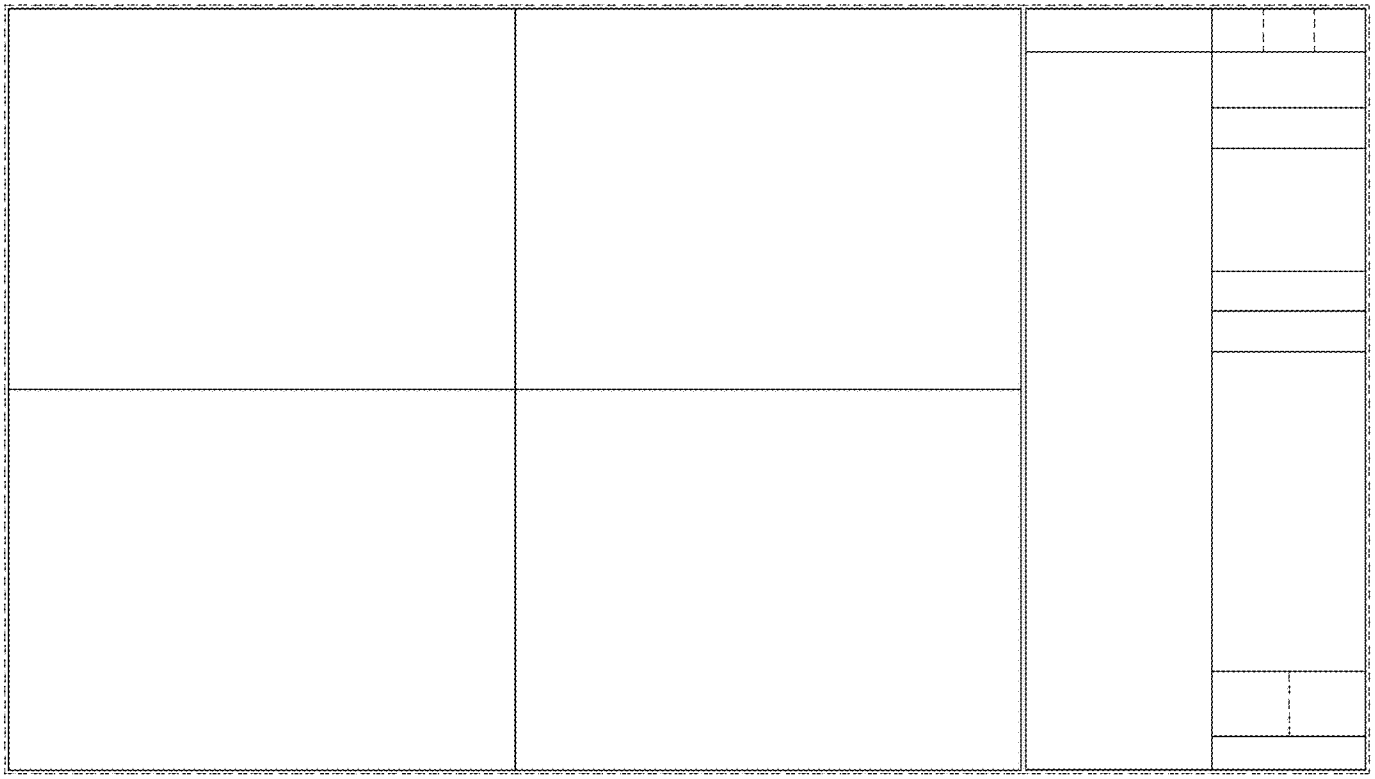
(AMENDED) FIG. 3

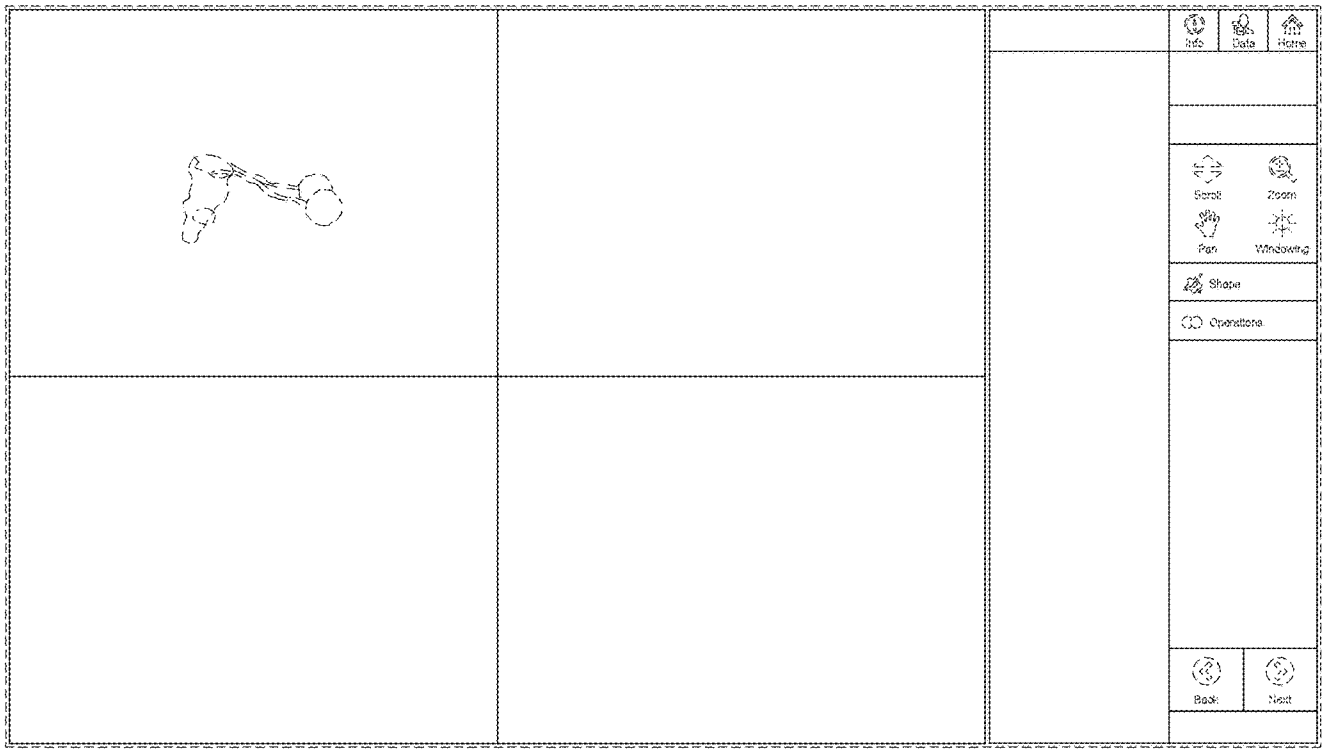
(AMENDED) FIG. 4

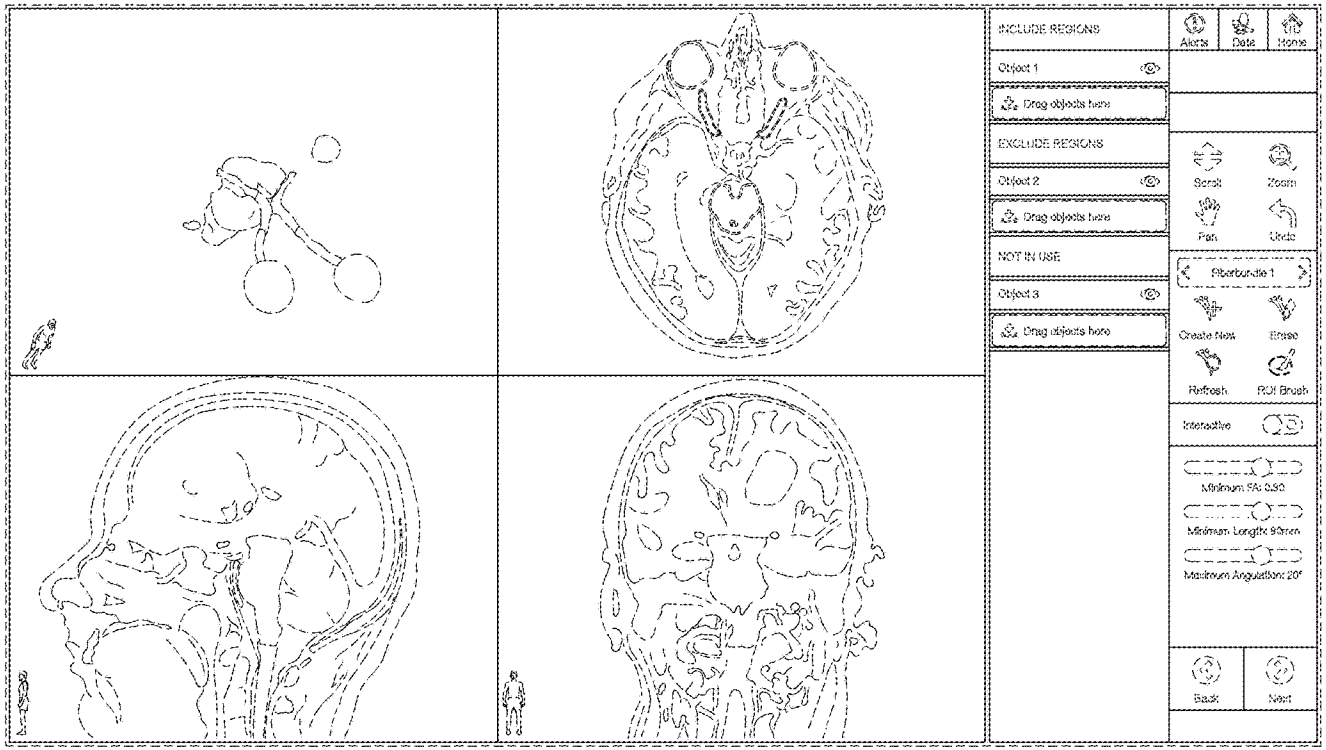
(AMENDED) FIG. 5

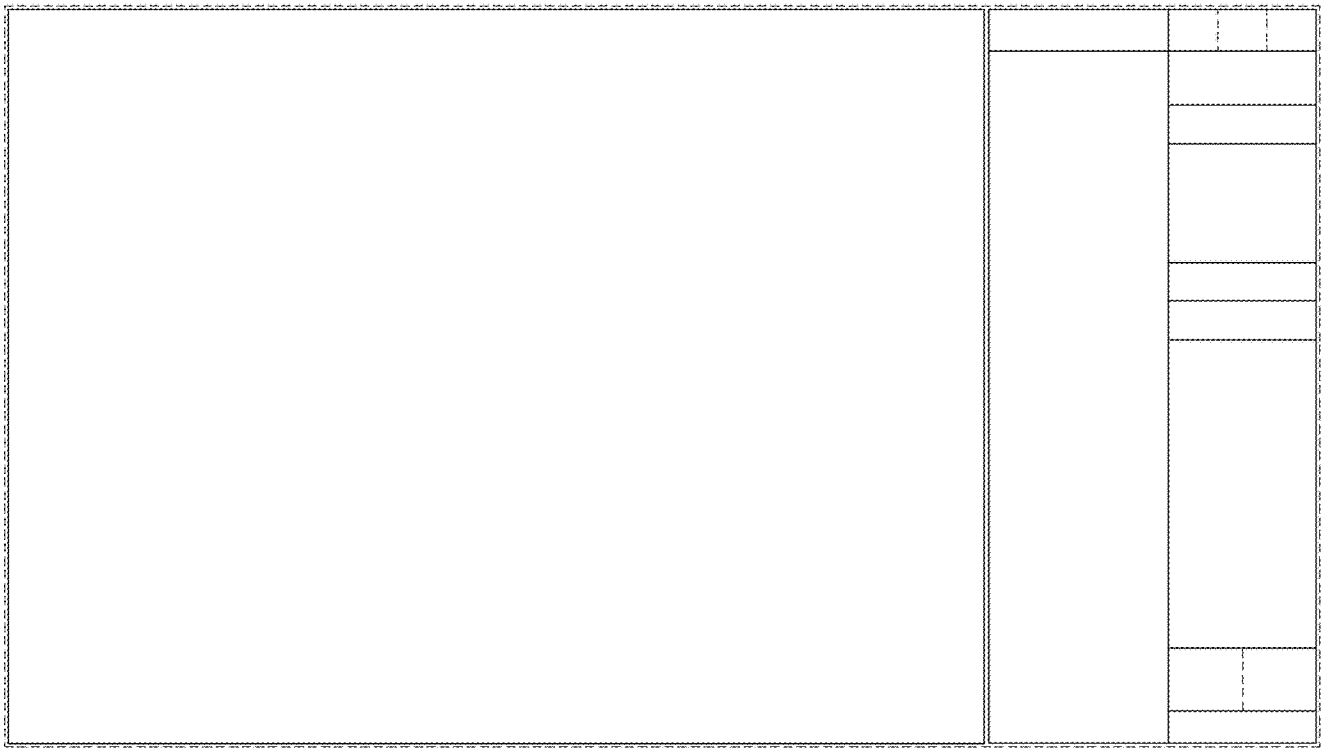
(AMENDED) FIG. 6

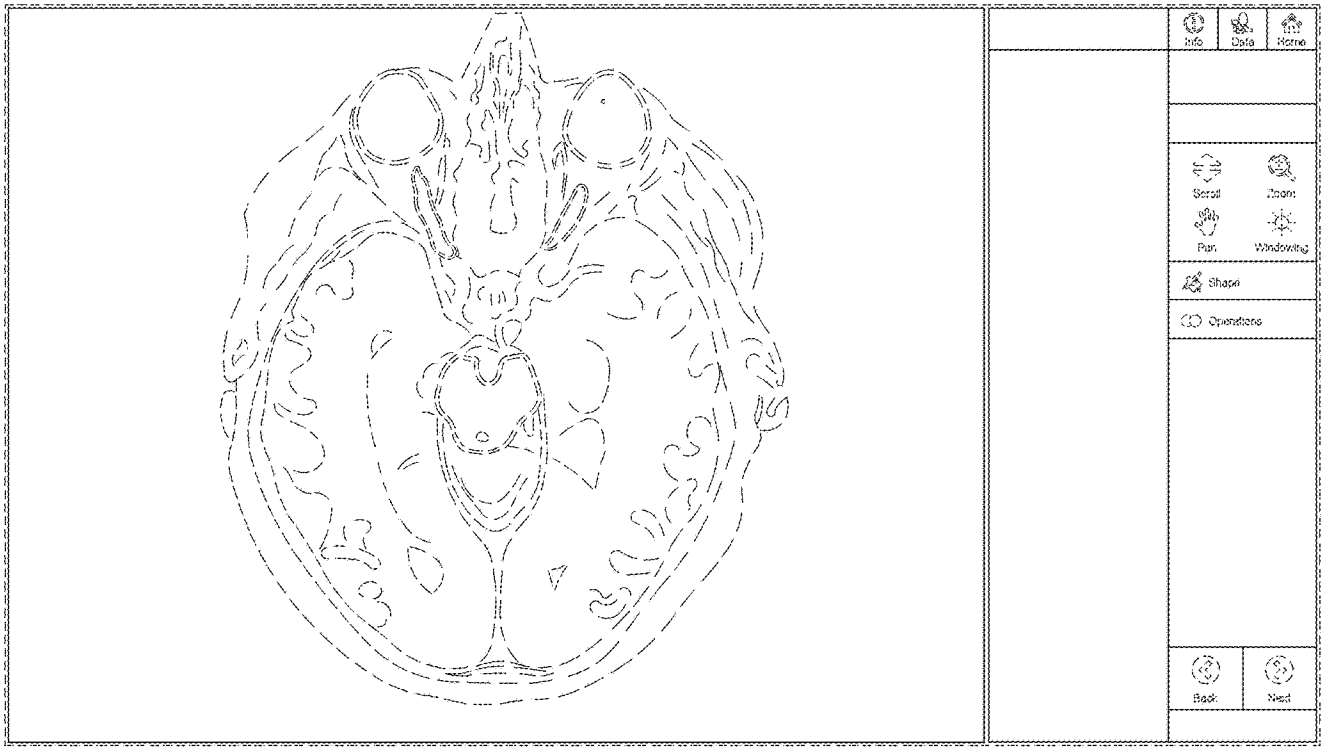
(AMENDED) FIG. 7